United States Patent [19]

Brüsewitz

[11] Patent Number: 4,675,298
[45] Date of Patent: Jun. 23, 1987

[54] PETRI DISH

[75] Inventor: Gerhard Brüsewitz, Bergisch-Gladbach, Fed. Rep. of Germany

[73] Assignee: Madaus & Co., Cologne, Fed. Rep. of Germany

[21] Appl. No.: 724,488

[22] Filed: Apr. 18, 1985

Related U.S. Application Data

[63] Continuation of Ser. No. 406,648, Sep. 9, 1982, abandoned.

[30] Foreign Application Priority Data

Sep. 21, 1981 [DE] Fed. Rep. of Germany ....... 3137495

[51] Int. Cl.$^4$ .............................................. C12M 1/22
[52] U.S. Cl. .................................... 435/298; 435/801; 422/102; 220/4 B; 220/366
[58] Field of Search ................ 435/34, 297, 298, 299, 435/801; 220/366, 8, 4 B; 422/102

[56] References Cited

U.S. PATENT DOCUMENTS

| 2,971,892 | 6/1958 | Carski | 435/298 |
| 3,158,553 | 11/1964 | Carski | 435/298 |
| 4,335,074 | 6/1982 | Bernas | 422/102 |

Primary Examiner—Raymond N. Jones
Assistant Examiner—Marianne M. Cintins
Attorney, Agent, or Firm—Felfe & Lynch

[57] ABSTRACT

The present invention provides a Petri dish, especially for culturing micro-organisms, comprising a circular lower dish and a cover loosely laid thereon. Projections are formed provided on the periphery of the inner surface of the cover and, matching depressions are formed on the rim of the lower dish. This permits adjusting a gap between the cover and dish for control of gas exchange between the interior of the Petri dish and the atmosphere.

4 Claims, 6 Drawing Figures

PETRI DISH

This application is a continuation of application Ser. No. 406,648, filed Aug. 9, 1982, now abandoned herewith.

BACKGROUND

The present invention is concerned with a Petri dish, especially for culturing micro-organisms having a bottom dish and a cover and providing means to control gas exchange between the interior of the Petri dish and the atmosphere.

In microbiological techniques, Petri dishes of various sizes and of differing diameter are used for culturing micro-organisms. Petri dishes with diameters of from 50 to 150 mm. and with edge heights of 14 to 20 mm. are conventional. The materials used for making Petri dishes include glass, synthetic resins and, less frequently, corrosion-resistant metals, transparent synthetic resin materials preferably being used.

Two types of Petri dishes are known, namely, those the covers of which have projections on their inner surface and those the covers of which are free of projections on the inner surfaces. The usual three small, about 1 to 2 mm. high nub-like projections lie on the flat edge of the lower dish and prevent the cover from lying closely upon the edge of the lower dish so that a slit is formed through which gas exchange is possible with the inner space of the Petri dish.

After pouring in a nutrient substrate, especially a gel-like nutrient substrate, gas exchange is important for the culturing process for drying the surface, for the gas exchange carbon dioxide:oxygen or of other volatile metabolic products and, in the case of anaerobic culture processes, for the removal of oxygen or of the oxygen-containing atmosphere or for the replacement thereof.

In the case of Petri dishes which do not have projections, so that the cover lies directly on the rim of the lower dish and gives a tight closure of the Petri dish, because of the absence of gas exchange, there are frequently difficulties in culturing micro-organisms. On the other hand, when the cover lies directly on the rim of the lower dish, drying out of the nutrient substrates or of the investigation material is very much lower in comparison with Petri dishes with projections so that, inter alia, the nutrient substrates in the Petri dishes can be kept much longer and remain usable for longer periods of time.

In the following, there is explained, with reference to a CSP-agar storage-stability test, the action of Petri dishes with and without projections on the bottom part of the cover.

The drying out of CSP-agar in Petri dishes was tested under various conditions, using Petri dishes with the dimensions of 90×20 mm. made of polystyrene with and without nub-like projections.

18.5 g. amounts of CSP-agar were poured into the Petri dishes and then kept for 1 day at ambient temperature prior to commencement of the experiment.

The agar Petri dishes with and without projections were then stored for 13 days under various conditions:
(1) unpacked at 4° C., 20° C. and 37° C.;
(2) batches of 5 dishes enclosed in Frappan, then packed in batches of 10 dishes in an MD-carton at 4° C., 20° C. and 37° C.;
(3) batches of 5 dishes in a Cellophane bag and then, again in batches of 10 dishes, in an MD-carton at 4° C., 20° C. and 37° C.

The weight of the agar was determined by weighing at the commencement and at the end of the testing.

The results obtained are summarised in the following Table:

| temperature | projections | packing | decrease of the agar weight in 13 days % loss | extrapolated to 50% loss (days) |
|---|---|---|---|---|
| 4° C. | + | — | 2.77 | 235 |
| | + | Frappan + carton | 0.69 | 942 |
| | + | Cellophane + carton | 2.58 | 252 |
| | — | — | 1.22 | 532 |
| | — | Frappan + carton | 0.15 | 4333 |
| | — | Cellophane + carton | 1.01 | 643 |
| 20° C. | + | — | 21.71 | 30 |
| | + | Frappan + carton | 6.33 | 103 |
| | + | Cellophane + carton | 7.40 | 88 |
| | — | — | 11.61 | 56 |
| | — | Frappan + carton | 2.22 | 293 |
| | — | Cellophane + carton | 5.89 | 110 |
| 37° C. | + | — | 62.70 | 10 |
| | + | Frappan + carton | 8.32 | 78 |
| | + | Cellophane + carton | 28.59 | 23 |
| | — | — | 34.45 | 19 |
| | — | Frappan + carton | 6.09 | 107 |
| | — | Cellophane + carton | 16.61 | 39 |

The above Table demonstrates the drying out storage stability of an agar nutrient media (CSP) in standard Petri dishes with and without projections under various conditions: temperatures of 4° C., 20° C. and 37° C. without packing and with packing in Frappan + carton and Cellophane + carton.

Extrapolation of the drying out losses to a theoretical limiting concentration of usability of 50% drying out loss gives, as can be seen, comparable values.

Not only the temperature conditions of the storage but also the packing and the presence or absence of projections on the Petri dishes have a decisive influence on the extent of the drying out of the agar.

With regard to the storage temperature, the low temperature of 4° gives the longest periods of storage stability. Unpacked Petri dishes have a theoretical storage period of 235 days at 4° C., 30 days at 20° C. and only 10 days at 37° C.

By omitting the projections, these times are lengthened to about twice as much, namely, 532, 56 and 19 days, respectively.

The packing brings about a further prolongation of the storage stability. This is greater in the case of Frappan-packed Petri dishes than in the case of Cellophane packing.

The best results were obtained, in each temperature group, in the case of nutrient media in Petri dishes without projections, enclosed in Frappan and packed into an MD carton. In this case, the theoretical storage stability period, even at 20° C., was still 293 days.

Water of condensation did not appear to any appreciable extent during the experimental period.

From these experiments, it follows that the storage of prepared nutrient media is mainly made difficult by two factors: drying out of nutrient agar in Petri dishes which are not firmly closed and the formation of water of condensation.

Drying out mainly takes place due to air exchange between the lower dish and the cover lying loosely thereupon. This possibility of air exchange is favoured by the presence of the three nub-like projections on the lower side of the cover, which serve as distance pieces and thus give rise to a narrow circular air gap. This air gap for the better aeration of the cultures during culturing and also for reducing the formation of water of condensation on the inner surface of the lid is frequently very advantageous.

However, under certain circumstances, for example comparatively long culturing times because of poor growth, it is only possible to use dishes with covers without projections since otherwise the drying out would have a disturbing effect.

The above-described experiments clearly demonstrate the influence of the projections acting as distance pieces on the drying out of the nutrient substrate.

It is an object of the present invention to avoid the use of two different types of Petri dishes and to provide a single Petri dish which enables not only a distancing by means of projections but also, if desired, a tight closure.

SUMMARY OF THE DISCLOSURE

Thus, according to the present invention, there is provided a Petri dish, especially for culturing microorganisms, comprising a lower dish with a peripheral dish wall, a cover loosely laid thereon, and several projections on one of the cover and rim surface of the dish wall and projecting generally parallel to the dish wall at least when the cover is on the dish. The other thereof has open depressions which are spaced correspondingly to the projections and are adapted thereto, with a slight oversize, with regard to shape and size.

Such a Petri dish is equally suitable for all cultures. If the lower dish and the cover are so oriented with regard to one another that the projections in the cover fully engage in the depressions of the lower dish, then there is a close fit of the bottom of the cover against the edge of the lower dish and the closure of the Petri dish thus achieved prevents gas exchange. If, on the other hand, a gas exchange is desired, then, by a slight rotation of the cover in relation to the lower dish, the projections are moved out of at least full engagement with the depressions so that they lie at least move toward the upper rim of the lower dish and serve as distance pieces between the cover and the rim of the lower dish.

According to a preferred embodiment of the present invention, the depressions are vertical grooves on the upright wall of the lower dish and the projections consist of radial ribs or of nub-like thickenings. The ribs or the nub like thickenings and the grooves can have an angular or rounded cross-section.

For the formation of a press-stud-like connection, the ribs or the nub like thickenings and the grooves can widen out downwardly. In this manner, a press-stud-like fixing is achieved in order to prevent too easy a displacement of the cover, for example when Petri dishes containing a nutrient medium are being stored prior to use.

According to another preferred embodiment of the present invention, the whole of the rim of the lower dish is obliquely serrated and the cover is provided, against its wall, with a circle of corresponding oblique serrations. The circle of oblique serrations is advantageously provided on the inner side of the vertical wall of the cover so that the vertical wall of the cover can be used for external holding and as a prevention against displacement of the cover. The substantially horizontal oblique flanks of the serrations have a gentle slope and are roughened or milled on their upper surface. Such a construction of the aeration and closure means of the Petri dishes permits a measuring of the gas exchange by any desired positioning of the size of the openings between the serrations of the cover and the lower dish displaced with regard to one another. The rim of the lower dish is advantageously provided with a scale marking on the oblique flank of at least one serration. This simplifies the adjustment of the desired size of opening.

BRIEF DESCRIPTION OF THE DRAWINGS

The accompanying drawings illustrate a number of embodiments of the present invention. In the drawings.

Figure 1:
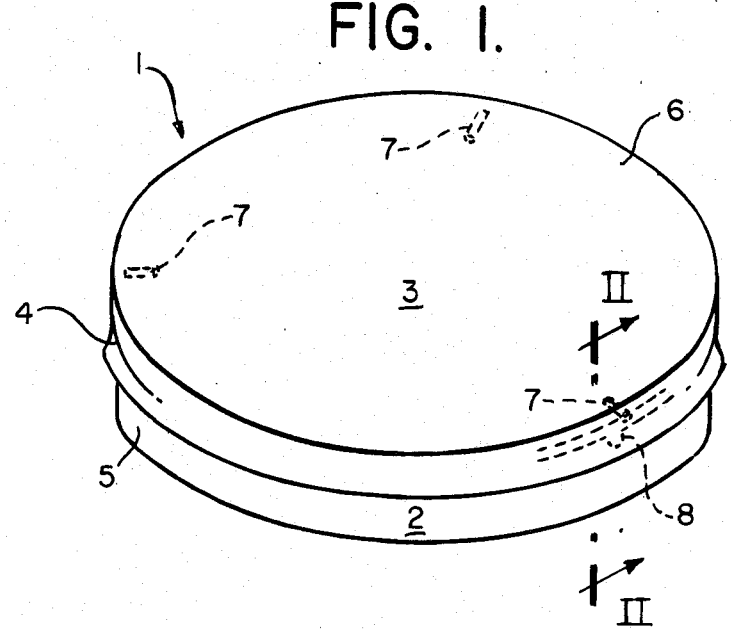
FIG. 1 is a perspective view of one embodiment of a Petri dish with the cover raised.
Figure 2:
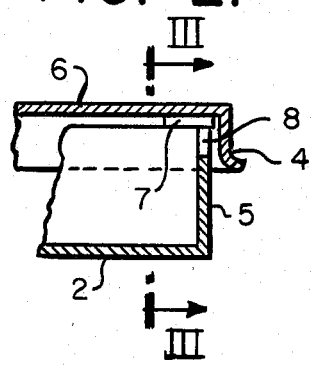
FIG. 2 is a section along the line II—II of FIG. 1.
Figure 3:
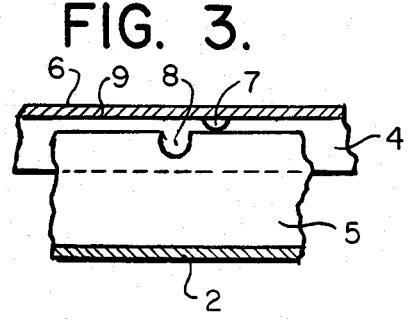
FIG. 3 is a section along the line III—III of FIG. 2.

A Petri dish 1 made of a suitable material, preferably transparent synthetic resin material or the like has a circular, cylindrical lower dish 2 and a matching cover 3 which is also of circular, cylindrical shape and sized to lie loosely on the lower dish 2. As shown in the drawings, the cover 3 includes a vertical wall 4 of which projects somewhat over the outer surface of vertical wall 5 of the lower dish 2. Cover 3 has a top 6 from which the vertical wall 4 extends. On the inner surface of cover top 6, there are arranged spaced apart, preferably, equidistantly, three nub-like projections 8 which are constructed as short radial ribs of rounded cross-section and are present in the region of the edge or rim of cover top 6 from which the wall 4 extends.

In the upper rim edge of the lower dish vertical wall 5, there are provided grooves 8 which are distributed in a manner corresponding one of said ribs 7, with a slight oversize, with regard to shape and size so that the ribs 7 can fittingly engage into the grooves 8.

Figure 4:
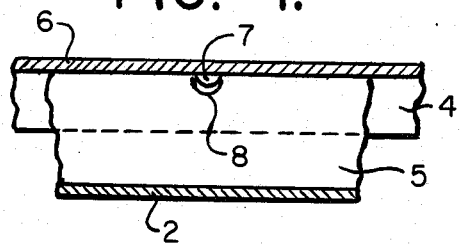
FIG. 4 is a section corresponding to FIG. 3 but with the cover lowered for closure of the Petri dish.

FIG. 4 illustrates the engaged state of the ribs 7 and the grooves 8 in cross-section with the under surface cover top 6 against the straight end edge face of the upper rim of the lower dish vertical wall 5.

As can be seen by the relationship of ribs 7 to grooves 8, a slight rotation of the cover 3 with respect to the lower dish 2 causes the ribs 7 to lift out of the grooves 8 and rest on the end edge face of the upper rim of lower dish vertical wall 5 to produce a gap 9 between the cover 3 and the lower dish 2, permitting a gas exchange with the inner space of the lower dish 2.

Figure 5:
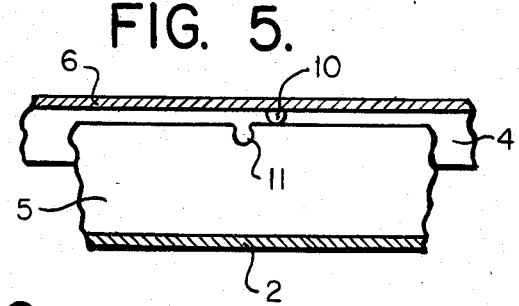
FIG. 5 is a cross-section through a Petri dish with a different form of projections and depressions.

In the embodiment illustrated in FIG. 5 the projections are bowed or bellied-out nub-like thickenings 10, a corresponding board or bellied-out widening also being present in the grooves 11. In the case of an engagement of the parts 10 and 11, there is produced a press-stud-like connection which prevents an unintentional displacement of the cover 3 with respect to the lower dish 2.

Figure 6:
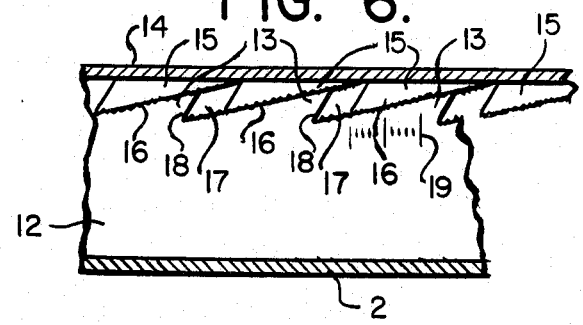
FIG. 6 is a cross-section through a Petri dish with yet another form of projections and depressions.

Whereas in the examples illustrated in FIGS. 1 to 5, projections and depressions adapted to one another are only shown at a few points, in the case of the embodiment illustrated in FIG. 6, the whole rim 12 of the lower dish 2 is provided all the way round with oblique serrations 13 and, correspondingly, the whole edge region of the cover 14 carries a circle of oblique serrations 15. The leading oblique flanks 16 of the serrations 13 and 15 run with a slight slope and are comparatively long. Furthermore, on their upper surface, they have millings which, by means of mutual gripping, bring about a securing of the cover 14 in the adjusted position. By means of a clockwise and anticlockwise rotation of the cover 14, the holes 17 between the vertical flanks 18 of the two serrations 13 and 15 become larger or smaller. When they lie against one another, the Petri dish is completely closed. The circle of serrations 15 on the cover is present inside the (not illustrated) outer wall of the cover 14, which serves as a holding edge when moving the cover. Scale markings 19 may be provided, for example on the rim 12 of lower dish 2 on the oblique flank 16 of at least one serration 13 to provide for reproducible adjustment between the cover 3 and the dish 2.

It will be understood that the specification and examples are illustrative but not limitative of the present invention and that other embodiments within the spirit and scope of the invention will suggest themselves to those skilled in the art. Thus, for example the projections can be on the lower dish and the grooves on the cover without departing from the scope of the invention.

What is claimed is:

1. In a petri dish having a dish and a cover sized to fit loosely over said dish to protect contents thereof, said dish having a dish wall defining the periphery thereof when said cover is on said dish, the improvement comprising:

projections disposed on one of said cover and dish wall having oblique serrations and being one of the radial ribs and nub-like projections projecting generally parallel to said dish wall at least when said cover is thereon;

grooved depressions having oblique serrations in the other of said cover and dish wall forming press-stud-like connections with said correspondingly sized projections; and means for spacing said projections and depressions correspondingly and sizing said depressions to receive said projections for adjustably spacing said dish wall and said cover by the rotational orientation thereof.

2. The petri dish of claim 1, wherein said cover has a cover wall extending about said dish wall when said cover is on said dish and said oblique serrations on said cover are on the inner side of said cover wall.

3. The petri dish of claim 1 or 6, wherein the engaging surfaces of at least one of said oblique serrations are roughened.

4. The petri dish of claim 3, and further comprising scale markings along at least one of said oblique serrations.

* * * * *

UNITED STATES PATENT AND TRADEMARK OFFICE
CERTIFICATE OF CORRECTION

PATENT NO. : 4,675,298
DATED : June 23, 1987
INVENTOR(S) : Gerhard Brusewitz

It is certified that error appears in the above-identified patent and that said Letters Patent is hereby corrected as shown below:

Col. 3, line 49, "move" should be -- more --.

Col. 6, line 8 (Claim 1), delete "the" after "of".

Col. 6, line 25 (Claim 3), "claim 1 or 6" should be

-- claim 1 or 2 --.

Signed and Sealed this

Third Day of May, 1988

Attest:

DONALD J. QUIGG

Attesting Officer

Commissioner of Patents and Trademarks